United States Patent [19]

Brossi et al.

[11] Patent Number: 5,171,750
[45] Date of Patent: Dec. 15, 1992

[54] SUBSTITUTED PHENSERINES AS SPECIFIC INHIBITORS OF ACETYLCHOLINESTERASE

[75] Inventors: Arnold Brossi, Bethesda, Md.; Malgarzota Brzostowska, Poznan, Poland; Stanley I. Rapoport, Washington, D.C.; Nigel Greig, Silver Spring; Xiao-shu He, Rockville, both of Md.

[73] Assignee: The United States of America as represented by the Department of Health and Human Services, Washington, D.C.

[21] Appl. No.: 765,746

[22] Filed: Sep. 26, 1991

[51] Int. Cl.⁵ .................. A61K 31/40; C07D 491/048
[52] U.S. Cl. ..................................... 514/411; 548/430
[58] Field of Search ................. 548/429, 430; 514/411

[56] References Cited

U.S. PATENT DOCUMENTS

| | | | |
|---|---|---|---|
| 4,791,107 | 12/1988 | Hamer et al. | 514/411 |
| 4,978,673 | 12/1990 | Meroni et al. | 514/411 |
| 5,081,117 | 1/1992 | Glamkowski et al. | 514/216 |

OTHER PUBLICATIONS

Robinson et al., J. Pharm. Pharmac., 1968, 20, Suppl., 213S-217S.
Albuquerque et al., Fundam. Appl. Caltoxicol., vol. 5, pp. 182-203 (1985).
Qian-Sheng Yu et al, Journal of Medical Chemistry, vol. 31, No. 12, Dec. 1988, pp. 2297-2300.
John R. Atack et al, The Journal of Pharmacology and Experimental Therapeutics, vol. 249, No. 1, Jan. 10, 1989, pp. 194-202.
Beilstein, Ed. II, vol. 23, 1954, p. 333.

Primary Examiner—Joseph Paul Brust
Assistant Examiner—MarySusan. Gabilan
Attorney, Agent, or Firm—Lowe, Price, LeBlanc & Becker

[57] ABSTRACT

The present invention relates to substituted phenylcarbamate or naphthylcarbamate tricyclic compounds which provide highly potent and selective cholinergic agonist and blocking activity and their use as pharmaceutical agents. The invention further relates to improvements in therapy relative to cholinergic diseases such as glacuoma, Myasthenia Gravis, Alzheimer's disease and to improvements in therapy and organophosphate poisoning. The invention further provides for a selective acetylcholinesterase and butyrylcholinesterase agents and a method for inhibiting these esterases.

14 Claims, No Drawings

SUBSTITUTED PHENSERINES AS SPECIFIC INHIBITORS OF ACETYLCHOLINESTERASE

TECHNICAL FIELD

The present invention relates to improvements in the treatment of diseases, and more particularly to compounds which exhibit selective inhibition of acetylcholinesterase and butyrylcholinesterase.

BACKGROUND ART

Physostigmine, also called eserine, and particular derivatives of physostigmine are anti-cholinesterase inhibitors which are well known. Such well known compounds are also useful in the treatment of glaucoma, Myasthenia, Gravis, Alzheimer's disease and as antidotes against poisoning with organophosphates.

Physostigmine was introduced into England in 1840 by Daniell (a British medical officer) in the form of the Calabar bean. The compound itself was first isolated by Jobst and Hesse in 1864. Physostigmine has been used as a treatment for glaucoma, and to reverse atropine-induced coma during the last century. Recent uses for this compound and its derivatives have been as effective antidotes to several drugs which possess central anticholinergic properties.

During the last two decades, studies related to the acetylcholine-receptor-ion-channel complex (AChR) of the neuromuscular junction have provided significant increases in knowledge of the receptor function. This membrane receptor has been readily available for study since nicotinic AChRs occur at very high densities in Torpedo and Electrophorus electric organs. Further, the understanding of the morphology and function of this receptor has been increased significantly by specific chemical probes for the different active sites of the receptor.

Nearly 20 years ago a significant discovery was made which helped in the study of this AChR. Alpha-bungarotoxin (Alpha-PGT) was obtained from snake venoms which binds irreversibly and specifically to the acetylcholine (ACh) recognition site on the nicotinic AChR. Alpha-PGT was such a highly selective probe that researchers were able to isolate and purify the different sub-units which comprise the nicotinic AChR. The sub-units were functionally reconstituted into artificial lipid membranes and were ultimately cloned.

Further sites on the nicotinic AChR were soon made available by the discovery of another class of toxins. These toxins were called histrionicotoxins and were isolated from the skin secretion of frogs in the family Dendrobatidae. The new sites available because of the hystrionicotoxins were discovered to be responsible for the allosteric alterations or non-competitive blockage of neuromuscular transmission. These sites are distinct from the against recognition site discovered through the alpha-PGT probe and are thought to be located on the ion channel component of the AChR.

Further, other drugs demonstrate the ability to modify non-competitively the activation of the AChR. Examples of such drugs are distinct and well known pharmacological agents which act on the peripheral nervous system as well as in the central nervous system. In particular, tricyclic anti-depressants, phenothiazine antipsychotics, the hallucinogenic agent Phencyclidine (PCP), local anesthetics, antimuscarinics, anticholinesterase agents and similar compounds to mention but a few.

Further ways for studying AChR are available due to microscopic kinetic models and biochemical rapid mixing methods to study permeability changes initiated by the binding of agonist molecules and conformational transitions of nicotinic receptor molecules.

The agonist recognition site at the nicotinic ACh receptor has been reported as having strong stereo specificity. This conclusion is based on the study of optical isomers of certain semi-rigid agonists, see for example Spivak et al., Mol. Pharmacol., Vol. 23, pages 337-343 (1983).

Conversely, the ion channel cites are apparently not stereo specific. This conclusion is based on the similar quantitative and qualitative actions of enantomers of perhydrohistrionicotoxin at the nicotinic AChR, see for example Spivak et al, FEBS Lett. Vol. 163, pages 189-193 (1983).

It has been discovered that the natural isomer of physostigmine has blocking properties as well as agonist properties at the neuromuscular AChR. By contrast (+)-physostigmine shows only negligible inhibition of cholinesterase (ChE). See Brossi et al., FEBS Lett., Vol. 201, pages 190-192 (1986).

Even though (+)-physostigmine has only negligible ChE inhibitory activity it is every effective as a protective pretreatment drug against multiple lethal doses of sarin, see Albuquerque et al, Fundam. Appl. Caltoxicol., Vol. 5, pages 182-203 (1985). The observed beneficial protection appears to be due to direct interactions of the carbamates with the postsynaptic nicotinic AChR. The protective effectiveness of the carbamates against organophosphates appears to be related to the direct ability of the carbamates to decrease the hyperactivation caused by accumulation of the neurotransmitter.

The above information, available due to the research in this field, is important in the evaluation of potential new pharmacological agents for treating cholinergic disorders, for example, Myasthenia Gravis and Alzheimer's disease. Potential agents can be evaluated for potency in vitro by testing the agents against electric EEL acetylcholinesterase (AChE) and human plasma butyrylcholinesterase (BChE).

Of the two enzymes known to hydrolyze acetylcholine (ACh) in vivo, AChE, which is found in red blood cells, in the brain and in nerve tissues, seems to be more specific than BChE which is found in serum, pancreas and in the liver. It, however, has not previously been shown in the art that compounds which selectively inhibit one of the two enzymes more than the other would offer a medical advantage. The natural alkaloid (−)-physostigmine, its potential metabolite (−)-(NI)-norphysostigmine, and the natural alkaloid physovenine which are used as biological standards in this art area inhibit AChE and BChE in vitro similarly at similar concentrations.

Accordingly, there is need in the art for highly selective agents active against one of AChE and BChE and not very potent against the other which may lead to better treatment of a particular cholinergic disorder and minimize negative side effects. Such compounds would be of great of medical importance in the treatment of cholinergic disorders.

SUMMARY OF THE INVENTION

It is an object of the present invention to overcome the difficulties in the prior art as set forth in the background of the invention.

It is another object of the present invention to provide highly potent and selective cholinergic agonist and blocking compounds.

It is a further object of the present invention to provide improvements in therapy relative to cholinergic diseases such as glaucoma, Myasthenia Gravis, Alzheimer's disease, and organophosphate poisoning.

It is a still further object of the present invention to provide compounds with selective acetylcholinesterase and butyrylcholinesterase activity.

It is a yet further object of the present invention to provide compounds having the following formula:

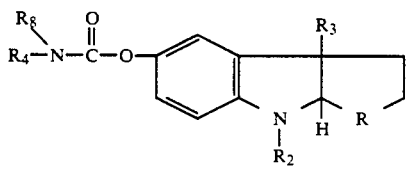

wherein
R is —O— or the group —N(—$R_1$)— and
$R_1$ is H or a —$C_1$-$C_{10}$-alkyl group;
$R_2$ and $R_3$ are independently selected from H or —$C_1$-$C_{10}$-alkyl;
$R_4$ is

or

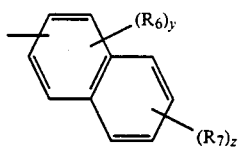

wherein
$R_5$, $R_6$ and $R_7$ are independently selected from H, halogen or —$C_1$-$C_{10}$ alkyl,
x is 0 or an integer from 1-5,
y is 0 or an integer from 1-3, and
z is 0 or an integer from 1-4; and
$R_8$ is H or $C_1$-$C_{10}$-alkyl;
including isomeric forms and pharmaceutically acceptable salts.

DESCRIPTION OF PREFERRED EMBODIMENTS

In accordance with this invention there are disclosed compounds of the formula

wherein
R is —O— or the group —N(—$R_1$)— and
$R_1$ is H or a —$C_1$-$C_{10}$-alkyl group;
$R_2$ and $R_3$ are independently selected from H or —$C_1$-$C_{10}$-alkyl;
$R_4$ is

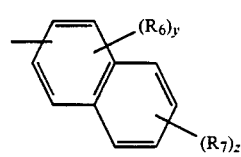

wherein
$R_5$, $R_6$ and $R_7$ are independently selected from H, halogen or —$C_1$-$C_{10}$ alkyl,
x is 0 or an integer from 1-5,
y is 0 or an integer from 1-3, and
z is 0 or an integer from 1-4, and
$R_8$ is H or —$C_1$-$C_{10}$-alkyl;
including isomeric forms and pharmaceutically acceptable salts.

Preferred are compounds according to Formula I having the Formula II:

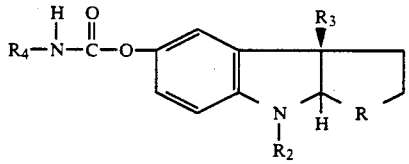

wherein
R is —O— or the group —N(—$R_1$)— and
$R_1$ is H or a —$C_1$-$C_{10}$-alkyl group;
$R_2$ and $R_3$ are independently selected from H or —$C_1$-$C_{10}$-alkyl; and
$R_4$ is

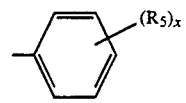

or

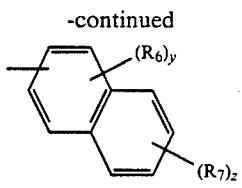

wherein
$R_5$, $R_6$ and $R_7$ are independently selected from H, halogen or —$C_1$-$C_{10}$ alkyl,
x is 0 or an integer from 1-5,
y is 0 or an integer from 1-3, and
z is 0 or an integer from 1-4;
including isomeric forms and pharmaceutically acceptable salts.

Further preferred are compounds according to Formula II having the following Formula III and IV:

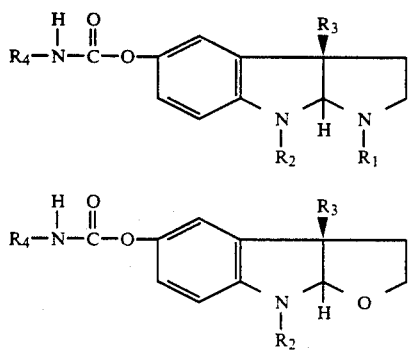

Still further preferred are compounds according to Formulas III and IV having the following Formula V and VI:

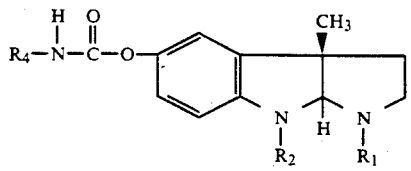

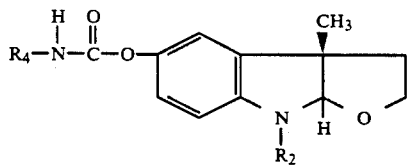

Yet further preferred are compounds according to Formula V having the following Formula VII

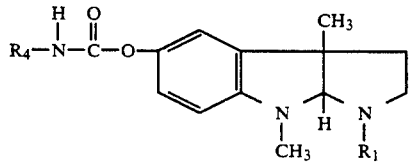

$R_1$-$R_7$ structures (where present) in the above Formulae III-VII are the same substituents defined above for Formula II.

Still further preferred are compounds of Formulae I-VII wherein x, y and z are 1 or 2. Even more preferred are compounds wherein x is 1 or 2 and $R_5$ is in the ortho and/or paraposition on the benzene ring. Particularly preferred $R_5$ groups are H, halogen and $C_1$-$C_5$ alkyl. Even more preferred $R_5$ groups are H, chloro, —$CH_3$, —$CH_2$—$CH_3$, —$CH_2$—$CH_2$—$CH_3$ and —CH(—$CH_3$)$_2$.

Preferred structures are set forth below wherein the main formula Roman numeral is further indicated with a lower case a, b, c or d in order to describe preferred groups for the $R_4$ substituent on each of the main formula which the Roman numerals alone represent, e.g., Ia-Id, IIa-IId, etc.:

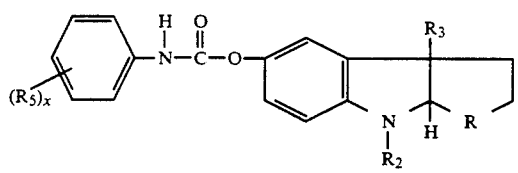

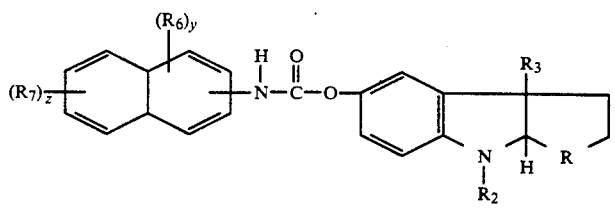

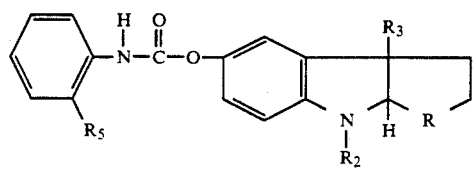

-continued
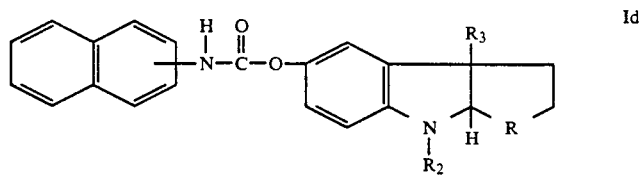 Id
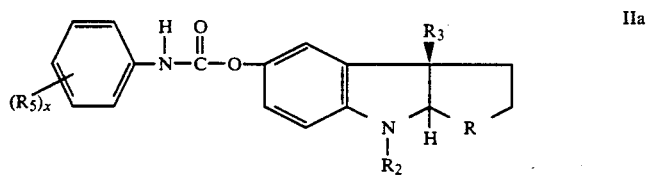 IIa
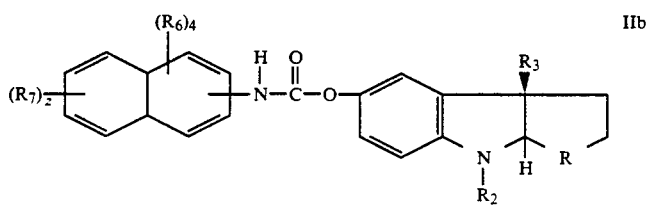 IIb
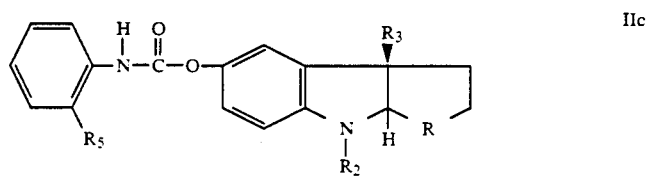 IIc
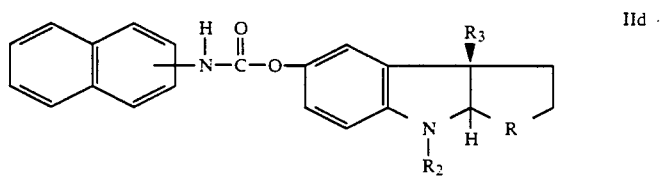 IId
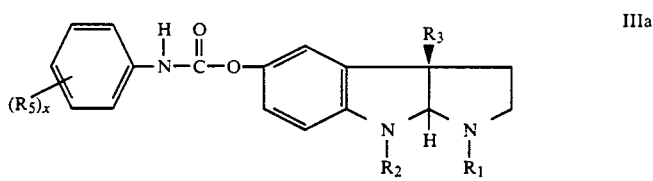 IIIa
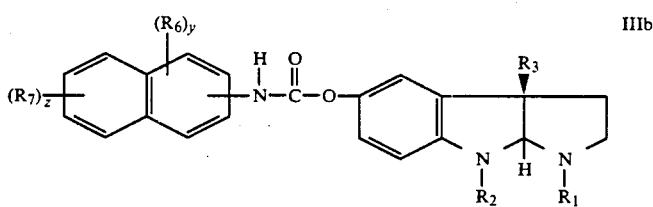 IIIb
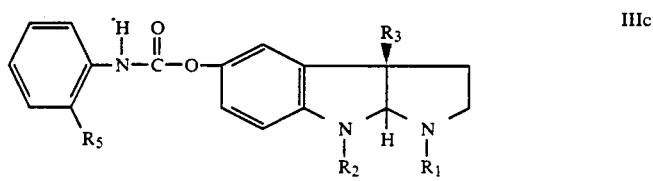 IIIc -continued
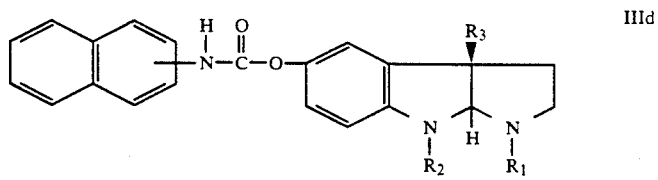 IIId
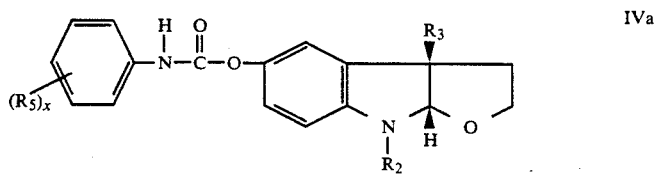 IVa
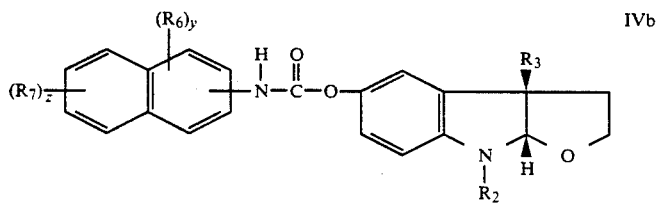 IVb
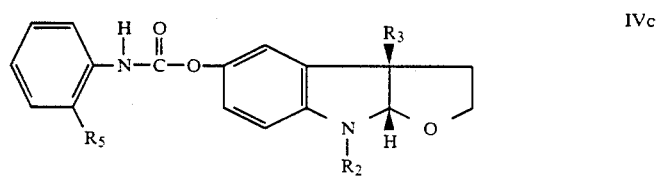 IVc
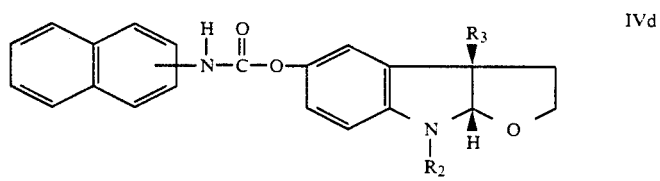 IVd
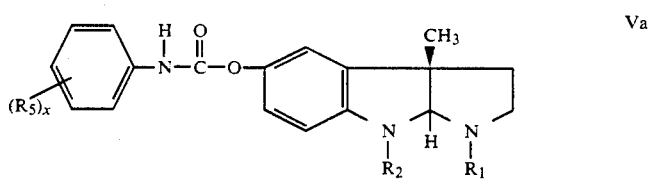 Va
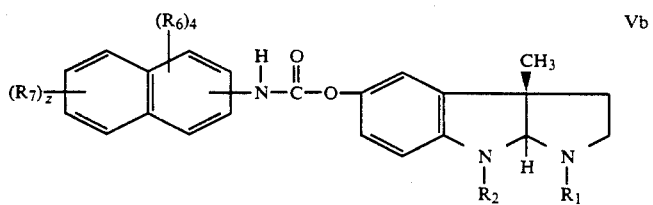 Vb
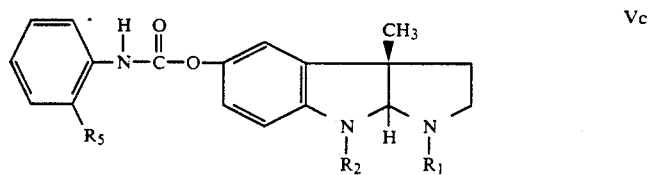 Vc -continued
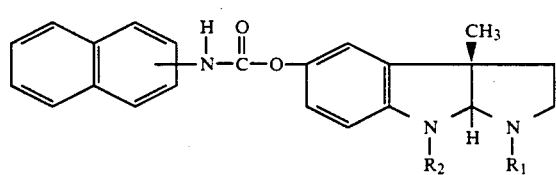
Vd
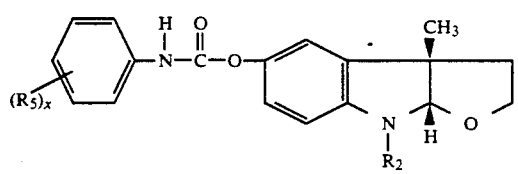
VIa
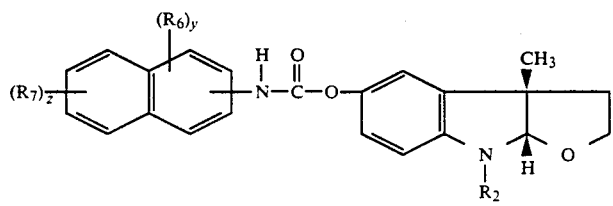
VIb
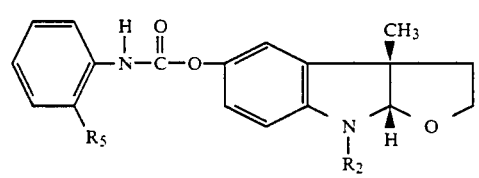
VIc
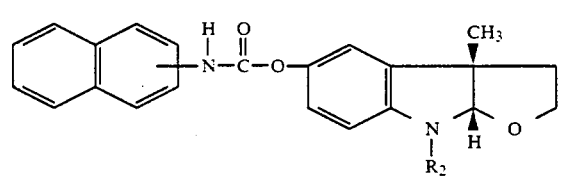
VId
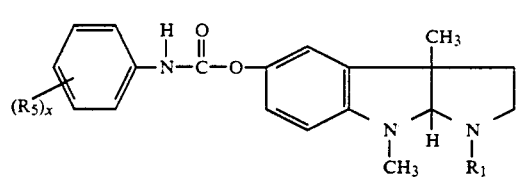
VIIa
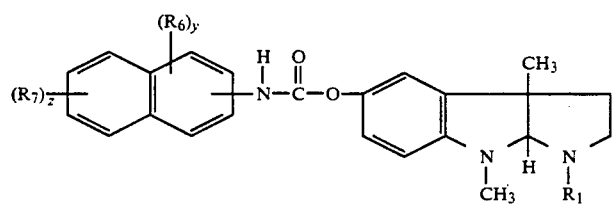
VIIb
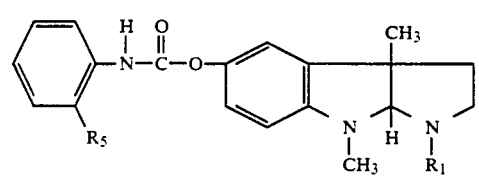
VIIc

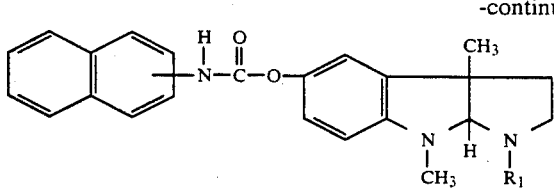

VIId

Also preferred are compounds according to the present invention in isomeric forms and pharmaceutically acceptable salts thereof. Pharmaceutically acceptable salts can be, for example, the alkali metal, alkali earth and ammonium salt. Further, pharmaceutically acceptable organic and inorganic acid addition salts may be used.

The compounds according to Formula I have asymmetric carbon atoms and can exist as optical isomers. For the purpose of this invention, the racemic mixtures and dextro and levo forms are included within the present invention. Hence, the particular dextro and levo rotary form or a particular isomer is sometimes indicated as a preferred optical isomer in particular formulae according to the invention.

Further, the above compounds according to the invention are useful as highly potent and selective cholinergic agonist and blocking pharmaceutical agents. Hence, the compounds of the present invention are useful in pharmaceutical compositions for systemic administration to human and animals in unit dosage forms, such as tablets, capsules, pills, powders, granules, suppositories, sterile parenteral solutions or suspensions, sterile non-parenteral solutions or suspensions, oral solutions or suspensions, oil and water or water in oil emulsions and the like, containing suitable quantities of the active ingredient. Topical application can be in the form of ointments, creams, lotions, jellies, sprays, douches, and the like. For oral administration either solid or fluid unit dosage forms can be prepared with the compounds of Formula I.

Compositions within the scope of the invention include compositions wherein the active ingredient is contained in an effective amount to achieve its intended purpose. The compounds can be administered in any pharmaceutically acceptable amount, for example, in amounts ranging from 0.001 gram to about 1 gram per kilogram of body weight. Based on the information which is presented herein, determination of effective amounts is well within the skill of the ordinary practitioner in the art. The compounds are generally useful in pharmaceutical compositions (wt%) of the active ingredient with a carrier or vehicle in the composition in about 0.1 to 99 wt % and preferably about 25-85 wt %.

Either fluid or solid unit dosage forms can be readily prepared for oral administration. For example, the compounds of Formula I can be admixed with conventional ingredients such as dicalcium phosphate, magnesium aluminum silicate, magnesium stearate, calcium sulfate, starch, talc, lactose, acacia, methyl cellulose and functional similar materials as pharmaceutical excipients or carriers. The compounds according to the invention can also be administered as water soluble salts such as salicylates, oxylates, and such like. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum or other inert oil can be encapsulated by making into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

Pharmaceutical compositions for parenteral and suppository administration can also be obtained using techniques standard in the art.

A preferred use of the compounds according to the invention is as pharmaceutical agents suitable for oral administration. Another preferred use of the compounds is in transdermal parenteral cholinergic agonist and blocking pharmaceutical preparations, which are particularly useful in treating cholinergic disorders such as glaucoma, Myasthenia Gravis, Alzheimer's disease, and organophosphate poisoning. Accordingly, compositions suitable for administration to these areas are particularly included within the invention. The above parenteral solutions or suspensions may be administered transdermally and, if desired, a more concentrated slow release form may be administered.

Accordingly, incorporation of the active compounds and a slow release matrix may be implemented for administering transdermally. The compounds may be administered transdermally at about 0.01 to 99% of the composition and preferably about 25 to 85 wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of blood-concentration vs. time profile, increased patient compliance due to elimination of multiple dosing schedules, bipassing the hepatic "first pass" metabolism, avoiding gastrointestinal incompatibilities and providing a predictable and extendable duration of activity. However, the main function of the skin is to act as a barrier to entering compounds. As a consequence, transdermal therapy has been preferred for a limited number of drugs that possess the desirable physiochemical properties for diffusion across the skin barrier. One effective method of overcoming the barrier function of the skin is to include a penetration enhancer in the formulation of the transdermal therapeutic system.

The penetration enhancer is a chemical compound that, when included in a formulation, temporarily increases the permeability of the skin to a drug line allowing more of the drug to be absorbed in a shorter period of time. Several different types of penetration enhancers have been reported such as dimethylsulfoxide, n-decyl methyl sulfoxide, N,N-dimethylacetamide N,N-dimethylformamide, 1-dodecylazacycloheptane-2-one (Azone), propylene glycol, ethanol, pyrrolidones such as N-methyl-2-pyrrolidone (NMP) and surfactants.

The above compounds can be present in the reservoir alone or in combination with pharmaceutical carriers. The pharmaceutical carriers acceptable for the purposes of this invention are the art known carriers that do not adversely effect the drug, the host, or the material comprising the drug delivery device. Suitable pharmaceutical carriers include sterile water; saline; dextrose; dextrose in water or saline; condensation products of castor oil and ethylene oxide combining about 30 to 35 moles of ethylene oxide per mole of castor oil; liquid acid; lower alkanols; oils such as corn oil; peanut oil; sesame oil and the like, with emulsifiers such as mono- or di-glyceride of a fatty acid; or a phosphatide, e.g., lecithin, and the like; glycols; polyalkylene glycols; aqueous media in the presence of a suspending agent, for example, sodium carboxymethyl cellulose; sodium alginate; poly(vinylpyrrolidone); and the like, alone, or with suitable dispensing agents such as lecithin; polyoxyethylene stearate; and the like. The carrier may also contain adjuvants such as preserving, stabilizing, wetting, emulsifying agents and the like together with the penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administered by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult human. The required dose is considerably less when administered parenterally, preferably about 0.01 to about 150 milligrams may be administered intramuscularly or transdermally, one or two times a day for an adult human.

Compounds of the present invention may be administered topically at about 0.01 to about 99 wt % of the composition, and preferably about 25 to 85 wt %. The present compounds are also useful in a method for treating cholinergic disorders such as glaucoma, Myasthenia Gravis, Alzheimer's disease, and as an antidote against poisoning with organo phosphates. The method according to the invention comprises some interesting effective amount of a compound according to the invention or an effective amount of a pharmaceutical composition according to the invention to a mammal in need of such treatment.

Surprisingly, the compounds according to the invention have shown selective cholinergic agonist and blocking activity. Of the two enzymes known to hydrolyze acetylcholine in vivo, acetylcholinesterase (AChE) which is found in red blood cells, in the brain, and in nerve tissues, seems to be more specific then butyrylcholinesterase (BChE) which is found in serum, pancreas and in the liver. It, however, was never shown that compounds which selectively inhibit one of the two enzymes more than the other, would offer a medical advantage.

The present invention relates to selective inhibition as follows. The natural alkaloid (−)-physostigmine, its potential metabolite (−)-(N1)-norphysostigmine and the natural alkaloid physovenine which were used as biological standards in the inhibited AChE and BChE in vitro similarly at similar concentrations.

These biological standard compounds used for comparitive purposes and derivatives having protective groups have the following structures.

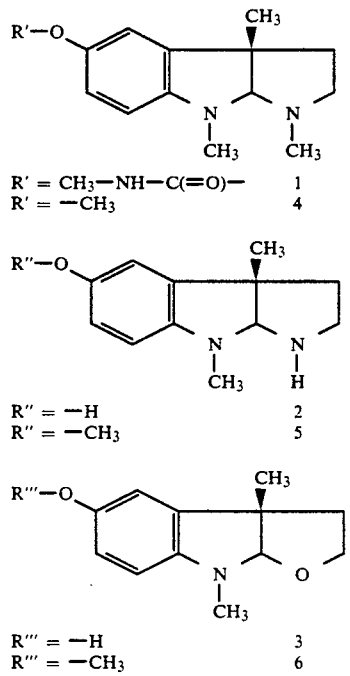

R' = CH₃—NH—C(=O)—  1
R' = —CH₃  4

R'' = —H  2
R'' = —CH₃  5

R''' = —H  3
R''' = —CH₃  6

The above structures are also used as starting materials to produce compounds according to the present invention.

The phenylcarbamate of (−)-eseroline and referred to in the literature as phenserine, however, was determined by the present invention experimentation to inhibit AChE from human erythrocytes in vitro at a 50-times lower concentration than BChE from human plasma. Accordingly, further derivatives were made and tested.

It was discovered according to the present invention that substituting the phenyl group in paraposition with a methyl group, a chlorine atom, or a methoxy group afforded derivatives which inhibited both enzymes at similar concentrations but such derivatives were considerably less potent than the biological standards described above. The phenylcarbamate of (−)-physovenol (22), also showed high preference for Ache (IC₅₀ for AChE=11, and for RChE=700), whereas the cumylcarbamate (4'-isopropylphenylcarbamate) (24) showed a reverse enzyme specificity (AChE=3800 and for BChE=16.5).

These above discoveries clearly indicated that selective inhibition of either AChE or BChE could be achieved by replacing the hydrogens on the phenyl group in phenylcarbamates with various substituents and inserting these modified phenylcarbamates on the basic core structure present in the three alkaloids that are the biological standards described above. The increased possibility of designing specifically acting inhibitors of AChE or BChE prompted an extension of these investigations and the results are the subject of the present invention.

The phenylcarbamates listed below in Table I and Table II were prepared from (—)-eseroline (4), (—)-Nl)-benzylnoreseroline (5) as the N-protected equivalent of (2), and from (—)-physovenol (6) which all have the natural (3aS)-absolute configuration (these numbers for the starting materials correspond to the numbers on the comparative structures and protected derivatives, whose structures are listed just previously in the above specification).

Reaction of these phenols with commercially available isocyanates in dry ether and in presence of a catalytic amount of sodium, afforded the desired carbamates. They were separated from "dimers" which invariably formed chromatography, and removed as the faster running materials. The structures of the carbamates which often were amorphous was secured by ms and $^1$H-nmr spectra, and they were characterized by tlc-analysis and by optical rotation. Details of the preparation of carbamates 7, 19 and 23 are given in the experimental section. Conversion of the (Nl)-benzyl-protected carbamates into compounds of the non-series was accomplished by catalytic hydrogenation over Pd(OH)$_2$ catalyst as described in the synthesis of 19.

Compounds according to the present invention, i.e., compounds 7-24, are listed in Table I and Table II below.

TABLE 1

| | R$_4$ | x | R$_1$ | R$_2$ | R$_5$ |
|---|---|---|---|---|---|
| 7 | (phenyl, (R$_5$)$_x$) | 1 | —CH$_3$ | —CH$_3$ | 2'-CH$_3$ |
| 8 | " | 2 | —CH$_3$ | —CH$_3$ | 2',4'-CH$_3$ |
| 9 | " | 1 | —CH$_3$ | —CH$_3$ | 4'-CH(CH$_3$)$_2$ |
| 10 | " | 1 | —CH$_3$ | —CH$_3$ | 4'-CH$_3$ |
| 11 | " | 2 | —CH$_3$ | —CH$_3$ | 2',6'-CH$_2$—CH$_3$ |
| 12 | " | 1 | —CH$_3$ | —CH$_3$ | 2'-CH$_2$—CH$_3$ |
| 13 | " | 1 | —CH$_3$ | —CH$_3$ | 2'-CH(—CH$_3$)$_2$ |
| 14 | " | 1 | —CH$_3$ | —CH$_3$ | H |
| 15 | " | 3 | —CH$_3$ | —CH$_3$ | 2',4',6'-CH$_3$ |
| 16 | naphthyl | — | —CH$_3$ | —CH$_3$ | — |
| 17 | (phenyl, (R$_5$)$_x$) | 1 | —CH$_3$ | —CH$_3$ | 2'-Cl |
| 18 | " | 2 | —CH$_3$ | —CH$_3$ | 2',6'-Cl |
| 19 | " | 1 | —H | —CH$_3$ | 2'-CH$_3$ |
| 20 | " | 2 | —H | —CH$_3$ | 2',4'-CH$_3$ |
| 21 | " | 1 | —H | —CH$_3$ | 4'-CH(—CH$_3$)$_2$ |

TABLE II

| | R | x | R$_2$ | R$_3$ | R$_5$ |
|---|---|---|---|---|---|
| 22 | —O— | 1 | —CH$_3$ | —CH$_3$ | H |
| 23 | " | 1 | —CH$_3$ | —CH$_3$ | 2'-CH$_3$ |
| 24 | " | 1 | —CH$_3$ | —CH$_3$ | 4'-CH(—CH$_3$)$_2$ |

Experimental

Melting points (uncorrected) Fisher-Johns apparatus; optical rotations ([α]$_D$, CHCl$_3$: Perkin-Elmer-241 MC automatic polarimeter, IR spectra (cm$^1$, CHCl$_3$) Beckman-IR-4230 instrument, BIO-RAD FTS-45 instrument; $^1$H NMR (in CDCl$_3$ with Me$_4$Si as internal reference, δ ppm, J Hz): Varian XL-300 MHz, Gemini 300 MHz spectrometer, MS (miz) for chemical ionization (CI) Finnigan-1015D mass spectrometer, for electron impact (EI): V. G. Micromass 7070 mass spectrometer, for HR MS (FAB): JEOL JMS-SX 102 magnetic sector mass spectrometer thin layer chromatography (silica gel GHL), 250 μm): Analtech Inc.; column chromatography (silica gel GHLF, 250 μm); Merck 60 (230–400 mesh); the solvent systems used for TLC analysis were the following: CH$_2$CL$_2$/5% MeOH; CH$_2$CL$_2$/10% MeOH; the solvent systems used for column chromatography: CH$_2$CL$_2$/5% MeOH(A); CH$_2$CL$_2$/10% MeOH(B).

(—)-2'-Methylphenylcarbamoyleseroline (7)

(—)-Eseroline (4) 0 (0.12 g, 0.55 mmol) was dissolved in anhydrous Et$_2$O (10 mL) and a small piece of Na metal was added. After stirring for about 2 min at room temperature under nitrogen, 2-methylphenylisocyanate (0.09 g, 0.70 mmol) was added dropwise. After complete addition the solvent was evaporated immediately. The residue was flask chromatographed on a silica gel column (system B) to give (7) as a foam (0.88 g, 46%); [α]$_D$—69.6° (c=0.5, CHCl$_3$), CI MS (miz): 352 (M+ +1); EI MS (miz): 351 (M+), HR MS (FAB) clacd for (M+ +1) C$_{21}$H$_{26}$N$_3$O$_2$ 352,2025, found 352,2020, IR; 3410, 2930, 1745; $^1$NMR 1.46 (s, 3 H, C10—CH$_3$), 1.90-2.12 (m 2 H, c#—H), 2.32 (s, 3 H, Mc-Ph), 2.55 (s, 3 H, Nl—CH$_3$, 2.58-2.70 (m, 2 H, C2—H$_2$), 2.91 (s, 3 H, n*—CH$_3$), 4.18 (s, 1 H, C9—H), 6.33 (d, J=8.4, 1 H, C7—H), 6.63 (br s, 1 H, N—H), 6.85-6.95 (m, 2 H, C4—H, C6—H), 7.05 (t, j=1 H, C5'—H), 7.15-7.23 (m, CH, CH3'—H, C6'—H), 7.85 (br s, 1 H, C4'—H).

All other carbamates: (—)-2'-4'-dimethylphenylcarbamoyleseroline (8), (—)-4'isopropylcarbamoyleseroline (9), (—)-4'-methylphenylarbamoyleseroline (10), (—)-2',6-diethylphenylcarbamoylescroline (11), (—)-2'-ethylphenylcarbamoyleseroline (12), (—)-2'isopropylphenylcarbamoyleseroline (13), (—)-phenylcarbamoyleserolne (14), (—)-(—)-2',4',6'-trimethylphenylcarbamoyleseroline (15), naphthylcarbamoyleseroline (16) , (—)-2'-chlorophenylcarbamoyleseroline (17) and (—)-2',6'-dichlorophenylcarbamoylseroline (18) were similarly prepared from (—)-eseroline (4) with the corresponding isocyanates and showed similar IR and NMR spectra to (7). The important data for these compounds is shown in Table III below.

(−)-2'Methylphenylcarbamoyl-Nl-Noreseroline (19)

The carbamates: (−)-2'methylphenylcarbamoyl-Nl-noreseroline (19), (−)-2',4'-dimethylphenylcarbamoyl-Nl-noreseroline (20) and (−)-4'-isopropylphenylcarbamoyl-Nl-noreseroline (21) were similarly prepared from (−)-(Nl)-benzylnoreseroline (5) instead of (4) by reacting (5) with the corresponding isocyanates compounds (20) and (21) showed similar IR and NMR spectra to compound (19). The important data for these compounds is shown in the Table III below.

(−)-5-O-(2'-Methylphenylcarbamoyl)physovenol (23)

(−)-Physovenol (6) (0.042 g. 0.20 mmol) was dissolved in anhydrous $Et_2O$ (8 mL) and a small piece of Na metal was added. After stirring for about 2 min at room temperature under nitrogen, 2-methylphenylisocyanate (0.032 g, 0.24 mmol) was added dropwise. After complete addition the reaction mixture was stirred at room temperature for an additional 1 h and then refluxed for 1.5 h. The solvent was evaporated and the residue was flash chromatographed on a silica gel column (system B) to give (23) as a foam (not TLC pure). This material was further purified by preparative HPLC on an Axiom silica column (5μ, 10×250 mm) using 1.5% MeOH in $CH_2Dl_2$ at a flow rate of 5 mL/min. The product thus obtained (0.03 g, 43%) as a foam was TLC pure: $[\alpha]_D -31.0°$ (c=1.0 $CHCl_3$), CI MS (ml%): 339 ($M^+ + 1$); EI MS (mix): 338 ($M^+$); IR: 3400 2950, 1740; $^1H$ NMR; 1.46 (s, eH, C10—$CH_3$), 1.95–2.20 (m, 2 H, C3—H), 2.32 (s, 3 H, C2'—$CH_3$), 2.91 (s, 3 H, N8—$CH_3$), 3.40–3.55 (ddd, j=5.3; 8.6; 11.0, 1 H, C2—H), 3.98 (dt, J=1.4; 8.6 H, C2—H), 5.10 (s, 1 H, C9—H), 6.31 (d, j=9.0, 1 H, C7—H), 6.55 (br s, 1 H, N—H), 6.85 (m, 2 H, C4—H, CGH), 7.05 (t, j=7.4 1 H, C5'—H), 7.13 (m, 2 H, C3'—H, c6'—H), 7.86 (br s, 1 H, C4'—H).

Compounds (22) and (24) were produced similarly to compound (23) by substituting phenylisocyanate and 4-isopropylphenylisocyanate, respectively, for the 2-methylisocyanate in the above procedure. Compounds (22) and (24) showed similar IR and NMR spectra to compound (23).

Table III below lists the important physical data for compounds according to the invention. The compound numbers in Table III correspond to the compound numbers in Table I and Table II.

TABLE III

| | $[\alpha]_D$ (°f.) (c = 1, $CHCl_3$) | mp (°C.) | CIMS (m/z) m ± + 1) | HRMS (FAB) m/z) ($M^+ = 1$) calcd (+)mmz | $^1H$ NMR |
|---|---|---|---|---|---|
| 8 | −79.6 | foam | 366 | | 2.28(s, 3H, C2-$CH_3$) |
| 9 | | | | | 2.29(s, 3H, C 4'-CH ($CH_3$) |
| 10 | −74.2 | 143–145 | 392 | $C_{21}H_{26}N_3O_2$ 3522025(−1.5) | 231(s, 3H, C4'-$CH_3$) |
| 11 | −36.1 | oil | 394 | $C_{24}$—$H_{32}N_3O_2$ 394,2495(+0.3) | 1.24(d, J= 7.4, 6H, 2-$CH_2$—$CH_3$) 2.68(m, 6H |
| 12 | −62.8 | foam | 366 | $C_{22}H_{18}N_3O_2$ 3662182(−0.3) | 1.26(d. J=7.5, 3H, $CH_2$—$CH_3$) 2.55- 2.78(M, 4H, C2-H, |
| 14 | −74.2 | 142–143 | 338 | | —$CH_2$—$CH_3$) 7.01(dJ= 7.4 1H, C4'-H), 7.2 (d, J= 7.4, 2H C3'- H, C5'-H) 734 (d, J=7.4 2H, C2' H, (6'-H) |
| 15 | −55.8 | foam | 380 | | 228(3s, CH, C2', C4' C6-$CH_3$ |
| 16 | −62.0 | foam | 388 | $C_{28}C_{26}N_3O_2$ 3882025(−1.6) | 7.51(m, 3H), 7.69(d, J= 8.1, 1H), 7.89(d, J= 7.5, 1H) 7.96 (d. J=7.9, 2H) |
| 17 | −67.2 | oil | 372 | | 7.02(dJ=7.8, C4'-H). |
| 18 | −66.2 | OIL | 406 | | 7.19(dJ=7.8, C4'-H), 7.39 (d, J=7.8, C3', C5'-H) |
| 19 | −60.7 C = 0.6 | 126–127 | 324($M^+$) | | |
| (24) | −54.6 | 167–169 | 397 | | 1.27(d, J=7.0, 2.90(m superimposed with N—$CH_3$, 4H. CH-iPr) |

In vitro assay of human anti-AChE and -BChE activity, IC50

A classical enzyme inhibition assay was undertaken to quantitate the activity of the derivatives against AChE and BChE. Anti-cholinesterase activity was determined against human erythrocyte AChE and plasma BChE in 0.1M $Na_3PO_4$ buffer (pH 8.0) using the spectrophotometric method of Ellman et al. (Biochem. Pharmacol. 7:88, 1961). Freshly collected plasma was diluted 1.125 with 0.1M $Na_3PO_4$ (pH 7.4) and lysed erythrocytes similarly diluted to 1:200 Acetyl-B-methylthiocholine (0.5 mM) and s-butyrylthiocholine (0.5 mM) were used as specific substrates for AChE and BChE, respectively, 25 ul of substrate and 25 ul of enzyme in a total volume of 0.75 ml.

Physostigmine derivatives, diluted in half log-intervals to a concentration range of between $1 \times 10^{-5}M$ and $3 \times 10^{-10}M$, were preincubated with enzyme (30 min at 21° C.) prior to addition of substrates. Following incubation (30 min at 37° C.), production of a yellow thionitrobenzoate anion was measured with a spectrophotometer set to 412 nm wavelength. Nonspecific substrate hydrolysis was determined under conditions of complete enzyme inhibition (by addition of physostigmine $1 \times 10^{-5}M$), and the associated change in absorbance subtracted from that observed with the test compounds. Finally, the activity of each compound was assessed alongside that of physostigmine, as an external standard, whose activity has been previously reported (Atack et al., J. Pharm. Expl. Ther. 249:294, 1989).

The AChE and BChE activity of each compound was expressed as an IC50, which is defined as the concentration in nmol required to inhibit 50% of enzyme activity (calculated as described by Atack et al., J. Pharm. Expl. Ther. 249:294, 1989)).

In vivo duration of activity studies

Catheters, filled with heparinized saline, were tied into the right femoral vein and artery of anesthetized male rats, which then were restrained in a plaster cast and allowed to recover from anesthesia in a temperature-controlled enclosure. Plasma samples were withdrawn to quantitrate untreated levels of AChE activity. At 90 min. after surgery, hexamethonium bromide (5 mg/kg, i.p.) was administered, followed by atropine methylbromide (4 mg/kg, s.c.) 10 min. later. These quaternary nicotinic and muscarinic antagonists, do not enter brain and inhibit peripheral cholinergic overdrive associated with cholinesterase inhibition, which may be deleterious to the animal. Two hours after surgery, either (i) physostigmine, (ii) physostigmine derivatives, or (III) THA was administered i.v. Plasma samples were removed at intervals between 2 min. and 8 hr., immediately frozen to $-70°0$ C. and then assayed for cholinesterase inhibition. AChE inhibition was measured as described above, with necessary modifications required for quantitation from rat plasma.

The $IC_{50}$ values for compounds according to the invention as compared to the prior art standards are provided in Table IV below. The compound numbers 7-24 refer to Examples 7-24 in Tables I and II.

TABLE IV

| Compound Number | AChE IC$_{50}$ (nM) | BChE IC$_{50}$ (nM) |
| --- | --- | --- |
| (1) (−)-physostigmne (comparitive std.) | 27.9 ± 2.4 | 16.0 ± 2.9 |
| (2) (−)-N(1)-Norphysostigmine (comparitive std.) | 21.0 ± 1.0 | 2.0 ± 1.0 |
| (3) (−)-physovenine (comparative std.) | 27.1 ± 0.8 | 3.5 ± 1.4 |
| Ex. 7 | 10.3 ± 1.6 | 1948.5 ± 245.5 |
| Ex. 8 | 13.6 ± 1.0 | 1817.0 ± 558.5 |
| Ex. 9 | 758.2 ± 21.2 | 51.3 ± 0.9 |
| Ex. 10 | 139.2 ± 3.7 | 251.1 ± 8.6 |
| Ex. 11 | 1493.7 ± 49.8 | 1073.5 ± 48.0 |
| Ex. 12 | 9.7 ± 0.1 | 2916.0 ± 537.0 |
| Ex. 14 | 24.0 ± 6.0 | 1300 |
| Ex. 15 | 1291.9 ± 73.8 | 3291.5 ± 885.0 |
| Ex. 17 | 496.0 ± 28.2 | 1607.9 ± 86.4 |
| Ex. 18 | 66.6 ± 1.8 | 424.6 ± 86.4 |
| Ex. 22 | 11.2 ± 2.1 | 700.0 ± 37.0 |
| Ex. 23 | 12.9 ± 0.8 | 1561.5 ± 119.8 |

The $IC_{50}$ values are means of between 2 and 8 assays, undertaken in duplicate.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

We claim:

1. A compound according to the Formula I

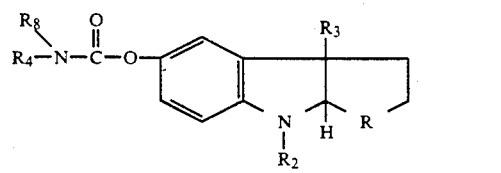

wherein R is —O— and
$R_2$ and $R_3$ are independently selected from H or —C$_1$-C$_{10}$-alkyl;
$R_4$ is

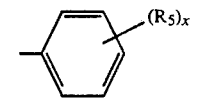

or

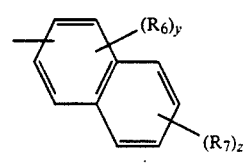

wherein
$R_5$, $R_6$ and $R_7$ are independently selected from H, halogen or —C$_1$-C$_{10}$ alkyl,
x is 0 or an integer from 1-5,
y is 0 or an integer from 1-3,
z is 0 or an integer from 1-4; and $R_8$ is H or —C$_1$-C$_{10}$-alkyl;
including isomeric forms, and
pharmacologically acceptable salts.

2. A compound according to claim 1, Formula I and having the Formula II

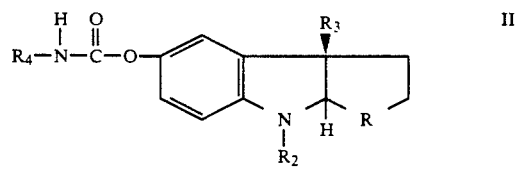

wherein
R is —O— and
$R_2$ and $R_3$ are independently selected from H, halogen or —C$_1$-C$_{10}$-alkyl; and
$R_4$ is

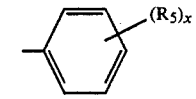

or

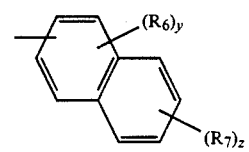

wherein $R_5$, $R_6$ and $R_7$ are independently selected from H or
—$C_1$-$C_{10}$ alkyl,
x is 0 or an integer from 1-5,
y is 0 or an integer from 1-3, and
z is 0 or an integer from 1-4;
including isomeric forms, and
pharmacologically acceptable salts.

3. A compound according to claim 1 having the formula IV wherein

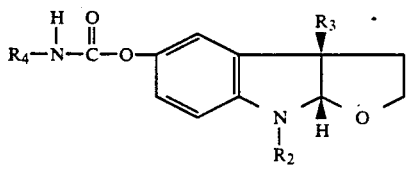

$R_2$ and $R_3$ are independently selected from H or —$C_1$-$C_{10}$-alkyl; and
$R_4$ is

or

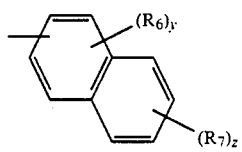

wherein
$R_5$, $R_6$ and $R_7$ are independently selected from H, halogen or —$C_1$-$C_{10}$ alkyl,
x is 0 or an integer from 1-5,
y is 0 or an integer from 1-3, and
z is 0 or an integer from 1-4;
including isomeric forms, and
pharmacologically acceptable salts.

4. A compound according to claim 3, wherein $R_3$ is a methyl group.

5. A compound according to claim 3, wherein $R_2$ and $R_3$ both represents a methyl group.

6. A compound according to claim 1, having the formula Ia

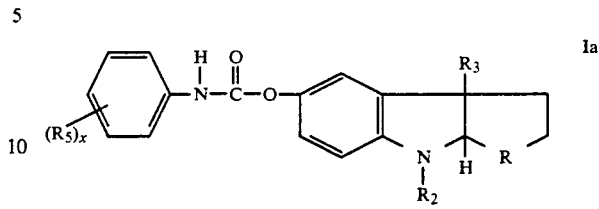

wherein
R is —O— and
$R_2$ and $R_3$ are independently selected from H or —$C_1$-$C_{10}$-alkyl; and
$R_5$ is independently selected from H, halogen or —$C_1$-$C_{10}$-alkyl and x is 0 or an integer from 1-5 including isomeric forms, and
pharmacologically acceptable salts.

7. A compound according to claim 6, where x is 1 or 2 and $R_5$ is in the ortho and/or para position.

8. A compound according to claim 6, wherein $R_5$ is independently selected from the group consisting of CHLORO, —$CH_3$, —$CH_2$—$CH_3$, and —$CH(-CH_3)_2$ and x is an integer from 1-5.

9. A pharmaceutical composition comprising a pharmaceutically effective amount of a compound according to claim 1 and a carrier.

10. A method for treating cholinergic disorders comprising administration of an effective amount of a compound according to claim 1 to a mammal in need of such treatment.

11. A method according to claim 10, wherein the cholinergic disorder is selected from the group consisting of glaucoma, Myasthenia Gravis, Alzheimer's disease.

12. A method for inhibiting acetylcholinesterase activity comprising administering an effective amount of a compound according to claim 1 to a mammal in need thereof.

13. A method for inhibiting butyrylcholinesterase activity in a mammal comprising administering an effective amount of a compound according to claim 1.

14. A method for treating organophosphate poisoning in a mammal comprising administering an effective amount of a compound according to claim 1.

* * * * *